United States Patent [19]

Polonsky

[11] Patent Number: 4,662,068
[45] Date of Patent: May 5, 1987

[54] SUTURE FUSING AND CUTTING APPARATUS

[76] Inventor: Eli Polonsky, 1608 S. Kenton, Aurora, Colo. 80012

[21] Appl. No.: 798,009

[22] Filed: Nov. 14, 1985

[51] Int. Cl.$^4$ .................. A61B 17/04; B26B 17/00
[52] U.S. Cl. .................. 30/124; 128/303.14; 128/335; 7/132; 7/170
[58] Field of Search .......... 128/303.13, 303.1, 303.14, 128/303.15, 303.16, 321, 305, 318, 334 C; 81/9.4, 9.44; 30/140, 124; 7/132, 125, 133, 158, 170; 228/54

[56] References Cited

U.S. PATENT DOCUMENTS 3,258,012 6/1966 Naykayama et al. ........... 128/334 C
3,354,478 10/1965 Allen ...................... 30/140

Primary Examiner—Richard C. Pinkham
Assistant Examiner—Gary Jackson
Attorney, Agent, or Firm—N. J. Aquilino

[57] ABSTRACT

A suture fusing and cutting apparatus having a forcep type instrument with jaws including a cutting edge and a fusing surface. The jaws are heated or otherwise stimulated by energy to sever and fuse plastic suture material when the jaws are closed on the suture.

2 Claims, 7 Drawing Figures

SUTURE FUSING AND CUTTING APPARATUS

BACKGROUND OF THE INVENTION

The present invention relates to sewing or suturing skin or tissues, and in particular, to apparatus that welds surgical sutures.

It is important that sutures be properly and evenly applied after a wound or an incision, to insure healing and to minimize scarring. In order to achieve these results, traditionally, much time and effort is needed for tying and cutting individual sutures after they are applied. Most often this work is done by hand which presents problems with access to the wound area particularly when working with deep tissue areas of the body. Often, the incision area is obscured which requires complicated time consuming manipulations to properly secure the suture. Surgical knots made in smooth suture materials such as nylon, require a minimum of three and often up to five individual manuevers to properly tighten them. Even then, they slip causing potential risks of bleeding, infection and wound disruption.

The present invention represents an advance in the art of suturing skin and tissue by providing an apparatus which welds surgical sutures after they are inserted in the tissue to be closed thereby eliminating both the tying and cutting steps heretofore required. The apparatus fuses the material solidly and reliably in one easy operation while still leaving the choice and size of the suture up to the surgeon. The degree of tension is still hand-controlled by the operator and he can be assured that there will be no risk of a knot becoming untied.

The apparatus includes a pair of forceps having a unique cutting and fusing face which are energized by a resistance heater or ultrasound power source controlled by a finger-operated switch. The interface of the forceps is provided with a cutting edge and a fusing edge whereby sutures may be severed and fused together in a single operation.

Among the objects of the present invention, is the provision of a hand-held suturing apparatus for severing and welding surgical sutures thereby eliminating the need for cutting and tying the same.

DESCRIPTION OF THE PREFERRED EMBODIMENTS

Figure 1:
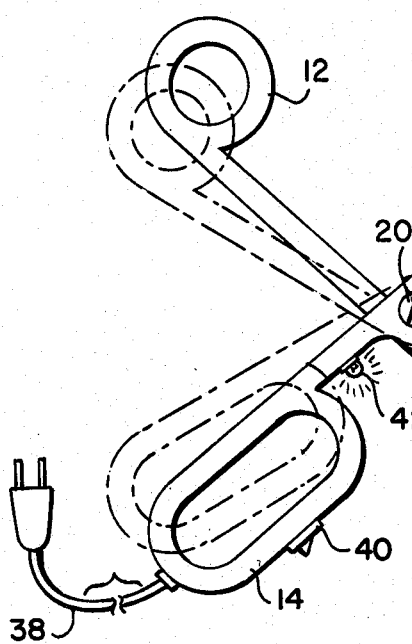
FIG. 1 is a view of the suture fusing and cutting apparatus of the present invention.

Referring to the drawings, FIG. 1 illustrates the suture fusing and cutting apparatus of the present invention including a forceps 10 having suitable handles 12 and 14 and arms 16 and 18 connected at a pivot 20. The forceps 10 includes a pair of jaws 20 and 22 at the end thereof. Each jaw has complementary opposite structure including cutting edges 24 and 26 and fusing surfaces 28 and 30 extending above the surface of the jaws.

Figure 2:
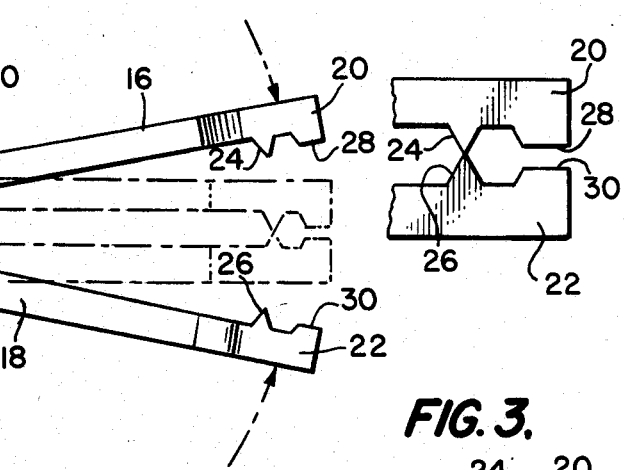
FIG. 2 is a partial view of FIG. 1.
Figure 3:
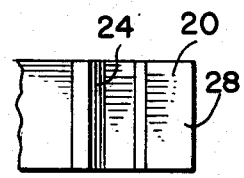
FIG. 3 is another partial view of FIG. 1.

FIG. 2 illustrates the jaws 20 and 22 in the closed position. It can be readily seen that the cutting edges 24 and 26 about each other at the point where the sharp edges terminate. As is evident from FIGS. 1-3, and particularly FIG. 3, cutting edges 24 and 26 are located in a plane perpendicular to the longitudinal axis of jaws 20 and 22. The fusing surfaces 28 and 30 do not touch when the jaws 20 and 22 are closed, but rather there is a space between each fusing surface 28 and 30. Thus, the fusing surfaces extend beyond the surface of the jaws 20 and 22 but in a plane below the upper edge of the cutting blades.

Figure 5:
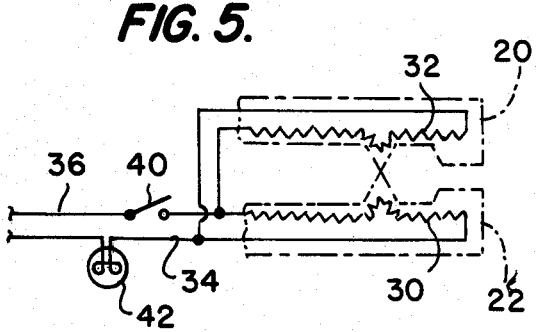
FIG. 5 is a partial schematic circuit of the invention of FIG. 1.

FIG. 5 illustrates a resistance heating circuit including resistance elements 30 and 32 in each of the jaws 20 and 22 respectively. The resistance elements 30 and 32 are connected to a pair of wires 34 and 36 to a suitable source of power. As shown in FIG. 1, the apparatus includes a power cord 38 which is used to connect the apparatus to the source of supply. The apparatus includes a switch 40 and a lamp 42 which provides an indication that the apparatus has current flowing through the resistance circuit.

Figure 4:
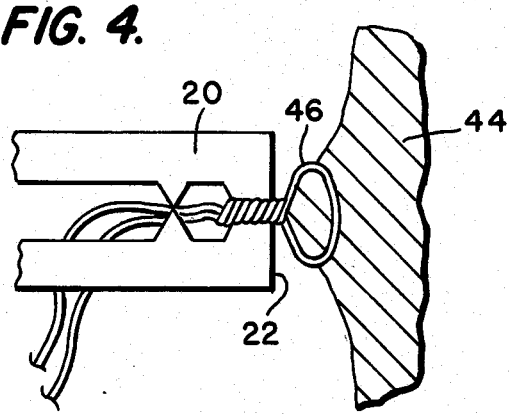
FIG. 4 is a partial view of the invention of FIG. 1 as it is used.

As shown in FIG. 4, a mass of living tissue 44 having an incision therein has been sutured using a typical heat deformable plastic suture 46 which typically would be connected to a needle and to a supply spool, both not shown. The strands of the suture 46 are preferably twisted together to tighten the suture. The amount of twisting will control the tension on the suture 46 thus enabling a practitioner to regulate the suturing procedure. With the jaws 20 and 22 heated by the internal resistance heater, closing of the jaws 20 and 22 will sever the strands of the suture 46 using the cutting edges 24 and 26 and fuse the strands together by heat using the fusing surfaces 28 and 30. This procedure is repeated for each suture taken and eliminates the need for difficult and time consuming tying of the suture.

Figure 6:
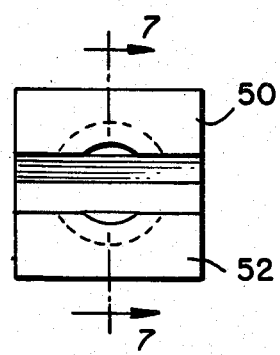
FIG. 6 is a partial view of a second embodiment of the invention.
Figure 7:
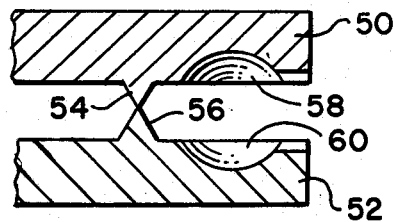
FIG. 7 is a partial sectional view taken along the line 7—7 of FIG. 6.

FIGS. 6 and 7 show jaws 50 and 52 of another embodiment of the apparatus of the present invention. In this embodiment, a pair of cutting edges 54 and 56 are used to sever the suture strand. A pair of hemispherical cavities 58 and 60 form the fusing surfaces. This sturcture will allow the suture strands to melt and form a bead in the cavities 58 and 60 which act as mold surfaces.

Other modifications may be made in the structure described without departing from the scope of the present invention as defined in the following claims.

I claim:

1. A suture fusing and cutting apparatus for simultaneously fusing and severing suture material comprising:
   a pair of longitudinal jaws, pivotably mounted and adapted to open and close in a complimentary manner relative to each other; said jaws including fusing surfaces and cutting edges thereon;
   said fusing surfaces carried by said jaws being spaced to create a gap therebetween when said jaws are in a closed position; said gap adapted to accommodate fusible material between said jaws for forming a bead of fusible material therebetween; said fusing surfaces being located adjacent the end of said longitudinal jaws;
   said cutting edges cooperating to sever suture material therebetween when said jaws are in a closed position; said cutting edges being located in a plane perpendicular to the longitudinal axis of said jaws;

and means for heating said jaws whereby, in use, closing of said jaws with fusible material therebetween causes said cutting edges to come together severing said fusible material simultaneously with fusing said material forming a bead with said fusing surfaces.

2. The apparatus of claim 1 wherein said fusing surfaces includes complimentary hemispherical cavities formed therein said cavities providing a molding surface for receiving said fusible material to form a bead thereof.

* * * * *